United States Patent
Ahmed et al.

(10) Patent No.: US 7,943,755 B2
(45) Date of Patent: May 17, 2011

(54) NEURON REGENERATION

(75) Inventors: Zubair Ahmed, Birmingham (GB); Martin Berry, Birmingham (GB); Ann Logan, Worcestershire (GB)

(73) Assignee: Neuregenix Limited, Birmingham (GB)

( * ) Notice: Subject to any disclaimer, the term of this patent is extended or adjusted under 35 U.S.C. 154(b) by 503 days.

(21) Appl. No.: 11/577,663

(22) PCT Filed: Oct. 22, 2004

(86) PCT No.: PCT/GB2004/004504
§ 371 (c)(1),
(2), (4) Date: Jul. 18, 2007

(87) PCT Pub. No.: WO2006/043014
PCT Pub. Date: Apr. 27, 2006

(65) Prior Publication Data
US 2008/0253989 A1 Oct. 16, 2008

(51) Int. Cl.
*C07H 21/04* (2006.01)
(52) U.S. Cl. .......... 536/24.5; 536/24.1; 536/24.31; 514/44; 435/6; 435/325; 435/375
(58) Field of Classification Search .......... None
See application file for complete search history.

(56) References Cited

U.S. PATENT DOCUMENTS

2003/0143732 A1* 7/2003 Fosnaugh et al. .......... 435/325
2004/0259247 A1* 12/2004 Tuschl et al. .......... 435/375

OTHER PUBLICATIONS

Turner et al. Antisense peptide nucleic acid-mediated knockdown of the p75 neurotrophin receptor delays motor neuron disease in mutant SOD1 transgenic mice. Journal of Neurochemistry 2003, pp. 752-763.*
Satoh et al. Cytokines and neurotrophic factors fail to affect Nogo-A mRNA expression in differentiated human neurones: implications for inflammation-related axonal regeneration in the central nervous system. Neuropathology and Applied Neurobiology 2002, vol. 28, pp. 95-106.*
Zhang et al. mRNA accessible site tagging (MAST): a novel high throughput method for selection effective antisense oligonucleotides. Nucleic Acid Research 2003, vol. 31: pp. 4-9.*
Horiuchi et al. Up-Regulation of Small GTPases, RhoA and RhoC, Is Associated with Tumor Progression in Ovarian Carcinoma. Laboratory Investigation 2003, vol. 83, No. 6: 861-870.*
Fournier et al. Rho kinase inhibition enhances axonal regneration in the injured CNS. Journal of Neuroscience, 2003: 1416-1423.*
Albrecht et al. Experimental Neurology 2002, vol. 173: 46-62.*
Ahmed, Zubair et al., Disinhibition of neurotrophin-induced dorsal root ganglion cell neurite outgrowth on CNS myelin by siRNA-mediated knockdown of NgR, p75NTR and Rho-A, Molecular and Cellular Neuroscience, 28 (2005) pp. 509-523, Elsevier Inc.
Ahmed, Z. et al, Enhancement of Retinal Ganglion Cell Regeneration by Downregulation of P75NTR Using Short Interfering RNA, Abstract, XP009047317, Site Design Programming © ScholarOne, Inc., http://sfn.scholarone.com/itin2003/main.html?new_page_id=126&abstract_id=12611&p_num..., date unknown.
Higuchi, Haruhisa et al, Functional inhibition of the p75 receptor using a small interfering RNA, XP-002329644, Science Direct, Biochemical and Biophysical Research Communications 301 (2003) pp. 804-809, Elsevier Science, 2003.

* cited by examiner

*Primary Examiner* — Kimberly Chong
(74) *Attorney, Agent, or Firm* — Michael Best & Friedrich LLP

(57) ABSTRACT

The invention provides a gene silencing molecule, which is adapted to down-regulate expression of a gene encoding a peptide involved with the Rho-A inhibitory pathway. The gene silencing molecule is used to promote neuron survival and axon regeneration in the central nervous system (CNS). The invention also provides compositions and methods of using same to improve neural survival and promote axonal growth.

14 Claims, 6 Drawing Sheets

Figure:1
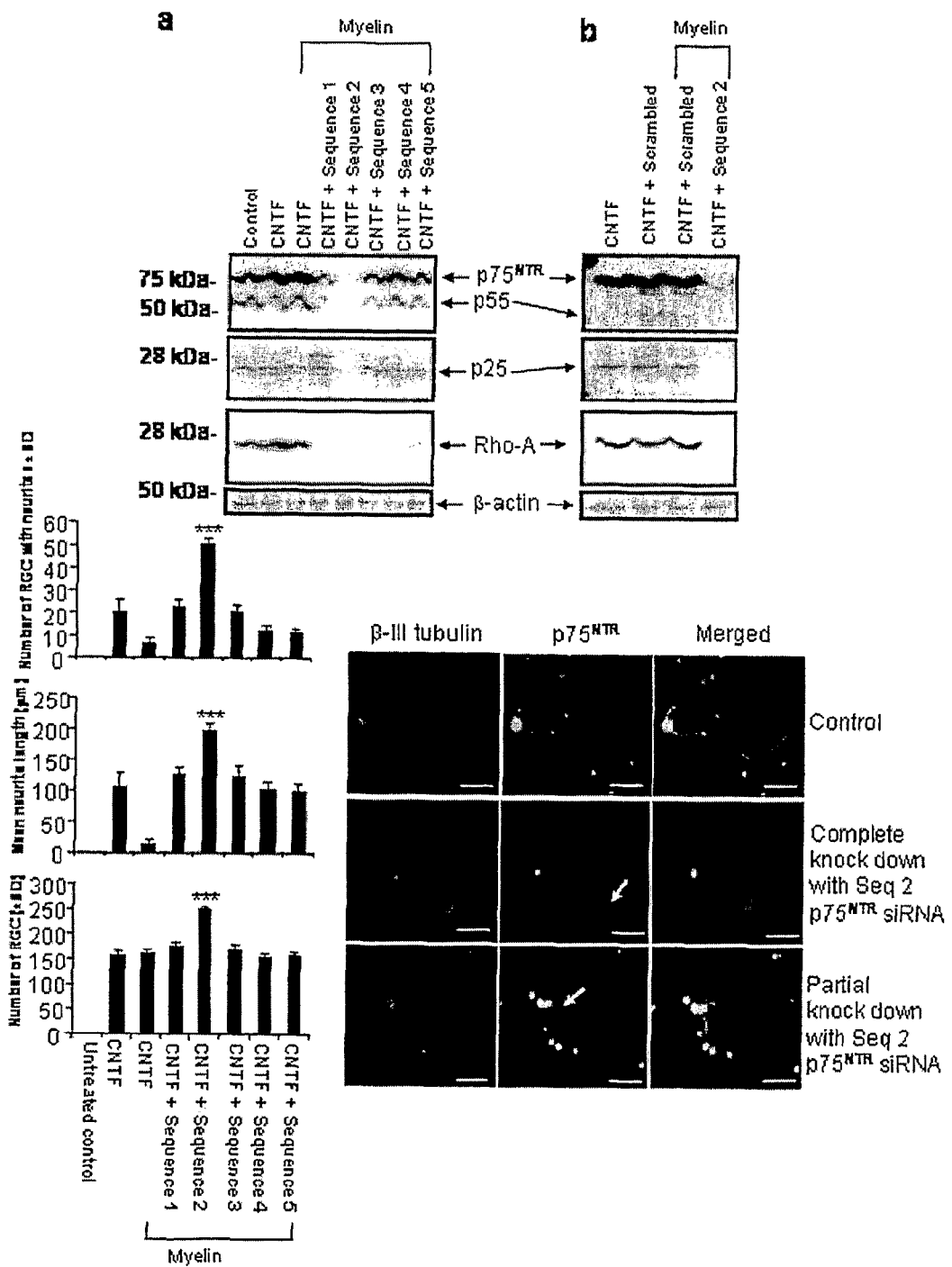

Figure:2
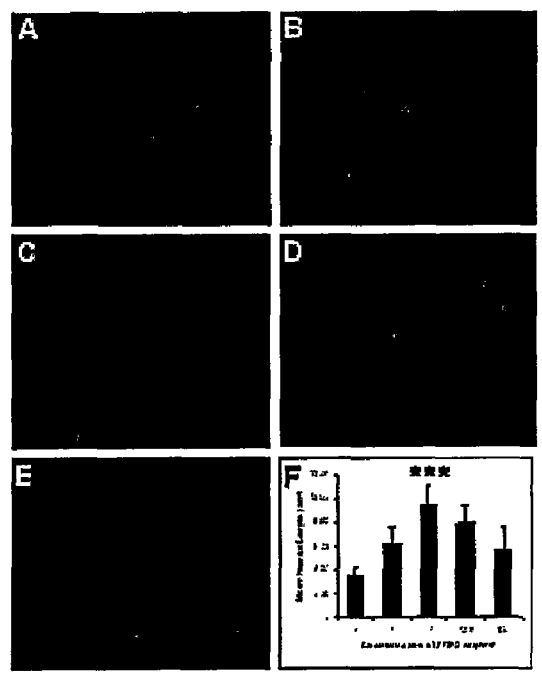
Figure:3
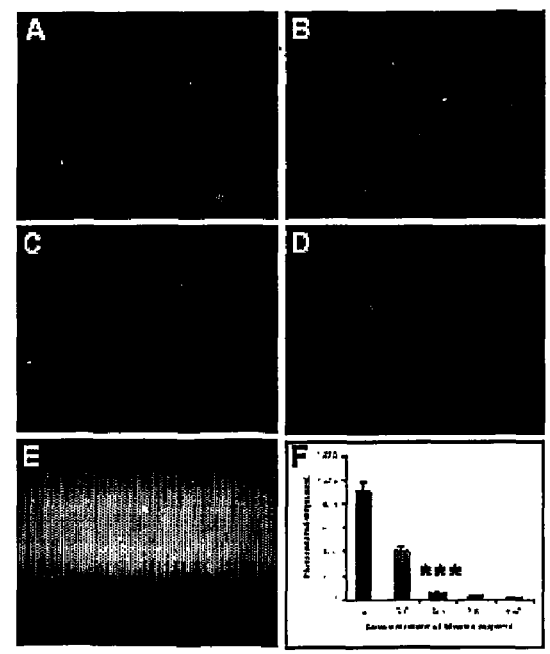

```
                       SEQUENCE LISTING

<160> NUMBER OF SEQ ID NOS: 18

<210> SEQ ID NO 1
<211> LENGTH: 21
<212> TYPE: DNA
<213> ORGANISM: Homo sapiens

<400> SEQUENCE: 1
aacctcattc ctgtctattg c                                              21

<210> SEQ ID NO 2
<211> LENGTH: 21
<212> TYPE: DNA
<213> ORGANISM: Homo sapiens

<400> SEQUENCE: 2
aacgcttgat gccctttag c                                               21

<210> SEQ ID NO 3
<211> LENGTH: 21
<212> TYPE: DNA
<213> ORGANISM: Homo sapiens

<400> SEQUENCE: 3
aagagaccag gagcattgta c                                              21

<210> SEQ ID NO 4
<211> LENGTH: 21
<212> TYPE: DNA
<213> ORGANISM: Homo sapiens

<400> SEQUENCE: 4
aagaaccaga gccatgcact c                                              21

<210> SEQ ID NO 5
<211> LENGTH: 21
<212> TYPE: DNA
```

-continued

```
<213> ORGANISM: Homo sapiens

<400> SEQUENCE: 5
aagcggagcg ctgacgccgg a                                              21

<210> SEQ ID NO 6
<211> LENGTH: 21
<212> TYPE: DNA
<213> ORGANISM: Homo sapiens

<400> SEQUENCE: 6
aatctcacca tcctgtggct g                                              21

<210> SEQ ID NO 7
<211> LENGTH: 21
<212> TYPE: DNA
<213> ORGANISM: Homo sapiens

<400> SEQUENCE: 7
aacctcacgc atctctttct g                                              21

<210> SEQ ID NO 8
<211> LENGTH: 21
<212> TYPE: DNA
<213> ORGANISM: Homo sapiens

<400> SEQUENCE: 8
aatcagctca ctgatgagga g                                              21

<210> SEQ ID NO 9
<211> LENGTH: 21
<212> TYPE: DNA
<213> ORGANISM: Homo sapiens

<400> SEQUENCE: 9
aaatgcactc aagggacgtg t                                              21

<210> SEQ ID NO 10
<211> LENGTH: 21
<212> TYPE: DNA
<213> ORGANISM: Homo sapiens

<400> SEQUENCE: 10
aatgactctc catttgggac t                                              21

<210> SEQ ID NO 11
<211> LENGTH: 21
<212> TYPE: DNA
<213> ORGANISM: Homo sapiens

<400> SEQUENCE: 11
aagattatga ccgtctgagg c                                              21

<210> SEQ ID NO 12
<211> LENGTH: 21
<212> TYPE: DNA
<213> ORGANISM: Homo sapiens

<400> SEQUENCE: 12
aaggatcttc ggaatgatga g                                              21

<210> SEQ ID NO 13
<211> LENGTH: 21
<212> TYPE: DNA
```

```
<213> ORGANISM: Homo sapiens

<400> SEQUENCE: 13
aaggcgggag ttagccaaaa t                                               21

<210> SEQ ID NO 14
<211> LENGTH: 21
<212> TYPE: DNA
<213> ORGANISM: Homo sapiens

<400> SEQUENCE: 14
aatgaagcag gagccggtaa a                                               21

<210> SEQ ID NO 15
<211> LENGTH: 21
<212> TYPE: DNA
<213> ORGANISM: Homo sapiens

<400> SEQUENCE: 15
aaagaccaaa gacggagtga g                                               21

<210> SEQ ID NO 16
<211> LENGTH: 21
<212> TYPE: DNA
<213> ORGANISM: Homo sapiens

<400> SEQUENCE: 16
aatcgcatgc gttccatttc g                                               21

<210> SEQ ID NO 17
<211> LENGTH: 21
<212> TYPE: DNA
<213> ORGANISM: Homo sapiens

<400> SEQUENCE: 17
aacttccacc atttggcggt c                                               21

<210> SEQ ID NO 18
<211> LENGTH: 21
<212> TYPE: DNA
<213> ORGANISM: Homo sapiens

<400> SEQUENCE: 18
aagagttcat ctgagtagga g                                               21
```

NEURON REGENERATION

CROSS-REFERENCE TO RELATED APPLICATIONS

This patent application is a national stage filing under 35 U.S.C. 371 of International Application No. PCT/GB2004/004504, filed 22 Oct. 2004, the disclosure of which is incorporated by reference herein in its entirety.

The present invention relates to neuron survival and axon regeneration, and particularly to the modulation of neural growth in the central nervous system (CNS). The invention also provides compositions and methods of using same to improve neural survival and promote axonal growth.

Axons and dendrites elongate profusely during development both in the CNS and peripheral nervous systems (PNS) of all animal species. However, in adults, axonal and dendritic regrowth in the CNS is increasingly lost with evolutionary progression. In the PNS, after infliction of a lesion, axons of all vertebrate species are able to regrow, at least to some extent. However, in the CNS of mammals, axon regrowth following damage is limited to axon sprouting. Regrowth of neuronal processes is, however, possible in the CNS of lower vertebrate species.

Glia are the decisive determinants for controlling axon regrowth. Mammalian glia are generally permissive for axon outgrowth in the CNS during development and in the adult PNS. Thus, upon infliction of a lesion, glia of the adult mammalian PNS can re-express their earlier axon outgrowth-promoting potential and foster regeneration. The CNS glia of some lower vertebrates remain permissive for axon regrowth in adulthood. In contrast, CNS glia of adult mammals do not re-express their developmental growth properties following lesions.

Neurotrophic factors (NTF) are present during the normal development of the nervous system. During such development, neuronal target structures produce limited amounts of specific NTFs necessary for the survival, differentiation and growth of the neurons projecting into target structures. NTFs promote the survival and/or maintenance of mature neurons and are primary determinants of neuronal regeneration after CNS injury. Furthermore, peripheral nerve glia (Schwann Cells) produce neurotrophic factors (NTF) which are presumed to be responsible for axon regeneration after injury in the adult PNS. However, long term experiments demonstrate that peripheral nerve implants grafted into the CNS do not maintain CNS axon regeneration beyond 30 days post lesion (dpl) and by 100 dpl most axons degenerate, presumably because Schwann cells in the peripheral nerve implants stop producing NTFs at about 20 days post-implantation, possibly due to a lack of axonal contact.

CNS myelin is a rich source of axon growth inhibitors, including myelin associated glycoprotein (MAG), oligodendrocyte myelin glycoprotein (OMgp), Nogo and, chondroitin sulphate proteoglycans (CSPG), which arrest axon growth by binding to the Nogo receptor (NgR). The Nogo receptor associates with LINGO-1 (LRR and Ig domain-containing Nogo receptor interacting protein) and p75 neurotrophin receptor ($p75^{NTR}$), a member of the tumour necrosis factor receptor family. The latter transduces inhibitory signals by activating downstream Rho-A, leading to sequential ROCK/LIM kinase/cofillin-mediated actin filament depolymerisation and growth cone collapse. Hence, NgR, $p75^{NTR}$, and the RhoA inhibitory molecule collectively form key elements of the axon growth inhibitory pathway. It will be appreciated that numerous other molecules, such as ROCK/LIM, cofillin and LINGO-1, are also involved in the pathway.

Despite numerous efforts spanning many years, neural regeneration in the CNS has never been achieved therapeutically. For instance, Logan et. al. (Eur. J. Neurosci. 1994 1 6(3) 355-63) investigated the effects of modulating levels of Transforming Growth Factor β1 ($TGF\beta_1$) in the injured CNS to see if neuron regeneration could be induced. $TGF\beta_1$ is a neurotrophic factor in some circumstances and is also a potent fibrogenic factor, stimulating the production of matrix molecules including CSPG (an axon growth inhibitory ligand), thereby potentially modulating the axon growth inhibitory pathway. They demonstrated that $TGF\beta_1$ participates in scar formation, which in turn restricts the growth of axonal projections in the injured CNS around the scarred region, probably by active axon growth inhibition via the inhibitory ligands like CSPG contained therein. They showed that blocking $TGF\beta_1$ activity did suppress scarring, but there was little or no associated axon growth, suggesting that blocking scar formation and the production of some categories of inhibitory molecules does not lead to enhanced axon regeneration.

Therefore, there is a distinct need to provide regenerative therapies that can promote neural growth in the CNS. Such therapies may be used to enable damaged or diseased nerves to survive, re-grow and function again following injury. The inventors therefore decided to focus their research on the neuron inhibitory pathway to see if modulation of this pathway could enhance NTF-stimulated neuron survival and axon outgrowth.

According to a first aspect of the present invention, there is provided a gene silencing molecule adapted to down-regulate expression of a gene encoding a peptide involved with the Rho-A inhibitory pathway.

According to a second aspect of the invention, there is provided a gene silencing molecule adapted to down-regulate expression of a gene encoding a peptide involved with the Rho-A inhibitory pathway for use as a medicament.

According to a third aspect of the present invention, there is provided use of a gene silencing molecule adapted to down-regulate expression of a gene encoding a protein involved with the Rho-A inhibitory pathway for the manufacture of a medicament for promoting neuron survival and axon growth.

The inventors investigated various biochemical pathways to assess whether or not they may be modulated to influence neuron growth. Their research established that the Rho-A inhibitory pathway was a surprisingly good target for modulation. By the expression "Rho-A inhibitory pathway", we mean the axon growth inhibitory pathway, which includes the NgR, $p75^{NTR}$, and RhoA inhibitory molecules, amongst others.

They went on to test various modulators of the Rho-A pathway, to see if axon growth could be promoted, although without success (for example, see above). However, surprisingly, use of gene silencing molecules (e.g. siNA) according to the first aspect of the invention did prove to be effective, and did stimulate neural growth. Furthermore, surprisingly, the inventors have established that the gene silencing molecules according to the present invention are also useful for promoting neuron survival (i.e. they reduce the clearance of neurons by apoptosis) Hence, the molecules of the first aspect have a medical use according to the second aspect, and more specifically have been shown to stimulate neuron survival and axon growth according to the third aspect.

It is preferred that the medicament is used to promote neuron survival and axon regeneration in the CNS. CNS injury may have resulted from surgery, trauma, compression, contusion, transection, neurotoxicity, or other physical injury, from vasculature pharmacologic or other insults including hemorrhagic or ischemic damage or from neurodegenerative or other neurological diseases. Ailments, characterised by impaired or failing axon growth, which may be treated by the medicament, are preferably characterised by neuronal injury. For instance, the ailment may be chronic or acute brain trauma, spinal cord injury, neurotoxicity, stroke, glaucoma, optic nerve damage, CNS haemorrhage, facial nerve injury, caused by elective surgery, nerve compression, concussion, ischaemia, burns and the like.

The inventors were most surprised to establish that molecules according to the invention can be used to treat conditions characterised by an increase in cell death. They have therefore established that the medicaments may also be used to treat conditions where neuron survival is a significant issue. For instance, the medicament may be used to treat neurodegenerative diseases such as dementia, Parkinson's Disease, Huntingdon's Disease, Alzheimers Disease, Motor Neuron Disease, CJD, and the like.

According to a fourth aspect of the present invention, there is provided use of a gene silencing molecule adapted to down-regulate expression of a gene encoding a protein involved with the Rho-A inhibitory pathway for the manufacture of a medicament for inhibiting cell apoptosis.

By the term "gene silencing molecule" we mean any molecule that interferes with the expression of the gene in question. Such molecules may be antisense molecules (antisense DNA or antisense RNA) or ribozyme molecules. Ribozymes and antisense molecules may be used to inhibit the transcription of the gene encoding a peptide involved with the Rho-A inhibitory pathway, or translation of the mRNA of that gene. Antisense molecules are oligonucleotides that bind in a sequence-specific manner to nucleic acids, such as DNA or RNA. When bound to mRNA that has a complimentary sequence, antisense RNA prevents translation of the mRNA. Triplex molecules refer to single antisense DNA strands that bind duplex DNA forming a colinear triplex molecule, thereby preventing transcription. Particularly useful antisense nucleotides and triplex molecules are ones that are complimentary to or bind the sense strand of DNA (or mRNA) that encodes a peptide involved with the Rho-A inhibitory pathway.

The expression of ribozymes, which are enzymatic RNA molecules capable of catalysing the specific cleavage of RNA substrates, may also be used to block protein translation. The mechanism of ribozyme action involves sequence specific hybridisation of the ribozyme molecule to complementary target RNA, followed by endonucleolytic cleavage, e.g. hammerhead motif ribozymes.

It is preferred that the gene silencing molecule is a short interfering nucleic acid (siNA).

It is preferred that the molecule according to the invention silences genes for NgR, p75$^{NTR}$ and/or the RhoA inhibitory molecule.

When the molecule is an siNA molecule, it may be double-stranded, and therefore comprises a sense and an antisense strand. The siNA molecule may comprise an siDNA molecule or an siRNA molecule. However, it is preferred that the siNA molecule comprises an siRNA molecule. Hence, the siNA molecule according to the invention preferably down-regulates gene expression by RNA interference (RNAi).

RNAi is the process of sequence specific post-transcriptional gene silencing in animals and plants. It uses small interfering RNA molecules (siRNA) that are double-stranded and homologous in sequence to the silenced (target) gene. Hence, sequence specific binding of the siRNA molecule with mRNAs produced by transcription of the target gene allows very specific targeted 'knockdown' of gene expression.

As one experimental approach, the inventors designed and produced a number of siRNA molecules with a view to testing their efficacy at modulating the Rho-A inhibitory pathway. Surprisingly, the inventors found that use of various siRNA molecules showing sequence specificity for various proteins involved with the Rho-A inhibitory pathway did result in disinhibition of that pathway, and resulted in improved axon growth and also improved neuron survival. This led them to believe that use of molecules according to the invention may be a useful technique for enhancing the endogenous mechanism of disinhibition of axon outgrowth and also improved neuron survival.

Genes encoding the peptide involved with the Rho-A inhibitory pathway may be referred to as target genes. Preferably, the siNA molecule is substantially identical with at least a region of the coding sequence of the target genes to enable down-regulation of the target genes. Preferably, the degree of identity between the sequence of the siNA molecule and the region of the target gene is at least 60% sequence identity, preferably, at least 75% sequence identity, preferably at least 85% identity; at least 90% identity; at least 95% identity; at least 97% identity; and most preferably, at least 99% identity.

Calculation of percentage identities between different amino acid/polypeptide/nucleic acid sequences may be carried out as follows. A multiple alignment is first generated by the ClustalX program (pairwise parameters: gap opening 10.0, gap extension 0.1, protein matrix Gonnet 250, DNA matrix IUB; multiple parameters: gap opening 10.0, gap extension 0.2, delay divergent sequences 30%, DNA transition weight 0.5, negative matrix off, protein matrix gonnet series, DNA weight IUB; Protein gap parameters, residue-specific penalties on, hydrophilic penalties on, hydrophilic residues GPSNDQERK, gap separation distance 4, end gap separation off). The percentage identity is then calculated from the multiple alignment as (N/T)*100, where N is the number of positions at which the two sequences share an identical residue, and T is the total number of positions compared. Alternatively, percentage identity can be calculated as (N/S)*100 where S is the length of the shorter sequence being compared. The amino acid/polypeptide/nucleic acid sequences may be synthesised de novo, or may be native amino acid/polypeptide/nucleic acid sequence, or a derivative thereof.

A substantially similar nucleotide sequence will be encoded by a sequence which hybridizes to any of the nucleic acid sequences referred to herein or their complements under stringent conditions. By stringent conditions, we mean the nucleotide hybridises to filter-bound DNA or RNA in 6× sodium chloride/sodium citrate (SSC) at approximately 45° C. followed by at least one wash in 0.2×SSC/0.1% SDS at approximately 5-65° C. Alternatively, a substantially similar polypeptide may differ by at least 1, but less than 5, 10, 20, 50 or 100 amino acids from the peptide sequences according to the present invention.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine; large non-polar, hydrophobic amino acids include phenylalanine, tryptophan and tyrosine; the polar neutral amino acids include serine, threonine, cysteine, asparagine and glutamine; the positively charged (basic) amino acids include lysine, arginine and histidine; and the negatively charged (acidic) amino acids include aspartic acid and glutamic acid.

The accurate alignment of protein or DNA sequences is a complex process, which has been investigated in detail by a number of researchers. Of particular importance is the trade-off between optimal matching of sequences and the introduction of gaps to obtain such a match. In the case of proteins, the means by which matches are scored is also of significance. The family of PAM matrices (e.g., Dayhoff, M. et al., 1978, Atlas of protein sequence and structure, Natl. Biomed. Res. Found.) and BLOSUM matrices quantify the nature and likelihood of conservative substitutions and are used in multiple alignment algorithms, although other, equally applicable matrices will be known to those skilled in the art. The popular multiple alignment program ClustalW, and its windows version ClustalX (Thompson et al., 1994, Nucleic Acids Research, 22, 4673-4680; Thompson et al., 1997, Nucleic Acids Research, 24, 4876-4882) are efficient ways to generate multiple alignments of proteins and DNA.

Frequently, automatically generated alignments require manual alignment, exploiting the trained user's knowledge of the protein family being studied, e.g., biological knowledge of key conserved sites. One such alignment editor programs is Align (http://www.gwdg.de/~dhepper/download/; Hepperle, D., 2001: Multicolor Sequence Alignment Editor. Institute of Freshwater Ecology and Inland Fisheries, 16775 Stechlin, Germany), although others, such as JalView or Cinema are also suitable.

Calculation of percentage identities between proteins occurs during the generation of multiple alignments by Clustal. However, these values need to be recalculated if the alignment has been manually improved, or for the deliberate comparison of two sequences. Programs that calculate this value for pairs of protein sequences within an alignment include PROTDIST within the PHYLIP phylogeny package (Felsenstein; http://evolution.gs.washington.edu/phylip.html) using the "Similarity Table" option as the model for amino acid substitution (P). For DNA/RNA, an identical option exists within the DNADIST program of PHYLIP.

In a preferred embodiment, the molecule is an siNA molecule and comprises between approximately 5 bp and 50 bp, more preferably between 10 bp and 35 bp, even more preferably, between 15 bp and 30 bp, and yet still more preferably, between 18 bp and 25 bp. It is preferred that the siNA molecule is between 20 bp and 23 bp, and more preferably the siNA molecule comprises 21 bp or 22 bp. Most preferably, the siNA molecule comprises less than 22 bp.

Design of a suitable siNA molecule is a complicated process, and involves very carefully analysing the sequence of the target mRNA molecule. Then, using considerable inventive endeavour, the inventors have to choose a defined sequence of siRNA which has a certain composition of nucleotide bases, which would have the required affinity and also stability to cause the RNA interference.

Hence, the coding sequence of the target gene was first scanned by the inventors to locate the target region thereof, which would encode the target mRNA, in order that a suitable sequence of siNA could be determined. Preferably, the target region of the target sequence comprises a diadenine start sequence, and a maximum of 60% GC content. Preferably, the molecule comprises less than 50% GC content. The antisense strand of the siNA molecule was designed with the DNA counterpart of the mRNA sequence of the target gene selected at the 5' end.

The siNA molecule may be either synthesised de novo, or produced by a micro-organism. For example, the siNA molecule may be produced by bacteria, for example, *E. coli*, in which case it is preferred that the 3' end of both the sense and the antisense strands of the siNA molecule may comprise an 8 nucleotide sequence 5'-CCTGTCTC-3'. This corresponds to the complementary sequence of the T7 promoter primer, required for efficient transcription of the siNA molecule. It is preferred that this 8 nucleotide sequence is removed prior to use of the siNA molecule to down-regulate the target gene.

Especially preferred siNA molecule sequences, which are adapted to down-regulate expression of the gene encoding the $p75^{NTR}$ receptor comprise the following sequences:—

```
p75^NTR sequences:-
Sequence 1,
5'-AACCTCATTCCTGTCTATTGC-3';       (SEQ ID No. 1)

Sequence 2,
5'-AACGCTTGATGCCCTTTTAGC-3';       (SEQ ID No. 2)

Sequence 3,
5'-AAGAGACCAGGAGCATTGTAC-3';       (SEQ ID No. 3)

Sequence 4,
5'-AAGAACCAGAGCCATGCACTC-3';       (SEQ ID No. 4)
and

Sequence 5,
5'-AAGCGGAGCGCTGACGCCGGA-3.        (SEQ ID No. 5)'
```

It should be appreciated that such siNAs may comprise uracil (siRNA) or thymine (siDNA).

The inventors tested each of these five siNA molecules by the methods as described in Example 1 and Example 2.

An important feature of the present invention is that gene silencing molecules according to the invention may be used in combination with a molecule, which simulates growth of neurites to have a surprising synergetic effect on axon growth and neuron survival. Used separately these agents have either modest or minimal effects whereas in combination the agents can dramatically improve neural regeneration. Examples of suitable growth stimulators may include any NTF (TRK dependent or TRK independent), for example, Ciliary Neurotrophic Factor (CNTF) or Fibroblast Growth Factor 2 (FGF2). It will be appreciated that CNTF is an effective growth stimulator of neurites in Retinal Ganglion Cells (RGC), and FGF2 is an effective growth stimulator of neurites in Dorsal Root Ganglia Neurites (DRGN). Other NTFs that may be used in conjunction with the molecules include NGF, NT-3, NT-4, BDNF, GDNF, FGF-1, FGF-5, CT-1, CDF, insulin, IGF-1, IGF-2, IL-6, LIF, NPF, PDGF, PN-1, S-100, TGF-β, and VIP (Oppenheim, 1996, Neuron 17:195-197).

Example 1 describes a test paradigm delivering the siNA molecules against $p75^{NTR}$ mRNA in cultured Retinal Ganglion Cells (RGC), which have been treated with CNTF in the presence of inhibitory CNS myelin. As shown in FIG. 1, the inventors found to their surprise that each of the above siNA molecules identified by SEQ ID No.1 to 5, in combination with CNTF, induced neuron survival and neuritogenesis in the RGCs in the presence of inhibitory CNS myelin. The extent of neuritogenesis caused by four of the five siNA molecules (all except SEQ ID No.2) was comparable to that induced in the absence of myelin and in the presence of CNTF. Each of the sequences exhibited dis-inhibition (i.e. counteracted the effects of the inhibitory myelin) of the neural outgrowth pathway, by down-regulating expression (otherwise known as knock-down) of the gene encoding $p75^{NTR}$ and thereby down-regulating its down-stream signaling components.

Even more surprisingly was that the siNA molecule having SEQ ID No.2 down-regulated $p75^{NTR}$ caused a significant increase in (a) the number of RGCs with neurites, and (b) the mean neurite length, and significantly promoted (c) RGC survival. Hence, not only did SEQ ID No.2 cause dis-inhibition of the pathway as did the other four siNA's, it was capable of inducing greater neural growth than would be stimulated in the absence of myelin. This was particularly surprising, as due to some unknown mechanism, SEQ ID No.2 was able to stimulate growth over and above that seen in the absence of myelin. This may be because the molecule was disinhibiting inhibitors other than myelin.

Hence, it is especially preferred that the siNA molecule comprises SEQ ID No.2 and particularly preferred that this molecule is combined with an NTF for clinical use.

It will be appreciated that SEQ ID No.2 comprises four consecutive thymine bases. The inventors initially considered this could be problematic in an RNAi regime. This was because they thought the four consecutive thymine bases in the siNA molecule could mimic a transcription termination sequence, thereby causing RNA polymerase to detach from the siNA template, terminating transcription of the siNA. Fortunately, this was not the case, and the preferred siNA not only may be efficiently synthesised in bacteria, but also is very effective at down-regulating $p75^{NTR}$.

Accordingly, the inventors have shown that siRNA-mediated knock down of $p75^{NTR}$ results in the disinhibition of CNTF-stimulated neurite outgrowth in RGCs.

The inventors carried out further tests on the same five siNA molecules. Example 2 describes delivering the same five siNA molecules against $p75^{NTR}$ mRNA in cultured Dorsal Root Ganglia Neurons (DRGN), which have been treated with FGF2 in the presence of inhibitory CNS myelin. It will be appreciated that FGF2 promotes neuritogenesis in DRGNs, and therefore acts as a positive growth stimulator of neurites in DRGNs. As above, CNS myelin acted to inhibit neuritogenesis. The inventors were surprised to find that each of the siNA molecules also increased cell survival and promoted axon growth in DRGNs, with the most effective siNA molecule having SEQ ID No.2. However, not only did SEQ ID No.2 cause disinhibition of the pathway as did the other four siNA's, it was also capable of inducing greater neural growth than would be stimulated in the absence of myelin. This was particularly surprising, as due to some unknown mechanism, SEQ ID No.2 was able to stimulate growth over and above that seen in the absence of myelin. This may be because the molecule was disinhibiting inhibitors other than myelin-related molecules.

Accordingly, the inventors have also demonstrated that siRNA-mediated knock down of $p75^{NTR}$ results in the disinhibition of FGF2-stimulated neurite outgrowth in DRGN.

Especially preferred siNA molecule sequences, which are adapted to down-regulate expression of the gene encoding NgR comprise the following sequences:—

```
NgR sequences:-
Sequence 1,
5'-AATCTCACCATCCTGTGGCTG-3';        (SEQ ID No. 6)

Sequence 2,
5'-AACCTCACGCATCTCTTTCTG-3';        (SEQ ID No. 7)

Sequence 3,
5'-AATCAGCTCACTGATGAGGAG-3';        (SEQ ID No. 8)

Sequence 4,
5'-AAATGCACTCAAGGGACGTGT-3';        (SEQ ID No. 9)
and

Sequence 5,
5'-AATGACTCTCCATTTGGGACT-3'.        (SEQ ID No. 10)
```

The inventors tested each of the above siNA molecules by the method as described in Example 2. Example 2 describes delivering the above five siNA molecules against NgR mRNA in cultured DRGNs, which have been treated with an NGF called Fibroblast Growth Factor 2 (FGF2) in the presence of inhibitory CNS myelin (growth inhibitor). The inventors found that each of the siNA molecules increased neuritogenesis in DRGNs, with the most effective siNA molecule having SEQ ID No.6. Surprisingly, SEQ ID No.6 stimulated more axon growth in the presence of inhibitory myelin than in the absence of myelin.

Hence, it is especially preferred that the siNA molecule comprises SEQ ID No.6.

Accordingly, the inventors have also demonstrated that siRNA-mediated knock down of NgR results in the disinhibition of FGF2-stimulated neurite outgrowth in DRGN.

Especially preferred siNA molecule sequences, which are adapted to down-regulate expression of the gene encoding the Rho-A molecule comprise the following sequences:—

```
Rho-A sequences:-
Sequence 1,
5'-AAGATTATGACCGTCTGAGGC-3';        (SEQ ID No. 11)

Sequence 2,
5'-AAGGATCTTCGGAATGATGAG-3';        (SEQ ID No. 12)

Sequence 3,
5'-AAGGCGGGAGTTAGCCAAAAT-3';        (SEQ ID No. 13)

Sequence 4,
5'-AATGAAGCAGGAGCCGGTAAA-3';        (SEQ ID No. 14)
and

Sequence 5,
5'-AAAGACCAAAGACGGAGTGAG-3'.        (SEQ ID No. 15)
```

The inventors tested each of the above siNA molecules by the method as described in Example 2. As above, the inventors found that each of the siNA molecules increased neuritogenesis in DRGNs, with the most effective siNA molecule having SEQ ID No.12. The inventors were surprised to find that each of the siNA molecules increased cell survival and promoted axon growth in DRGNs, with the most effective siNA molecule having SEQ ID No.2. However, not only did SEQ ID No.12 cause dis-inhibition of the pathway (as did the other siNAs), it was also capable of inducing greater neural growth than would be stimulated in the absence of myelin. This was particularly surprising, as due to some unknown mechanism, SEQ ID No.12 also appeared to be able to stimulate growth over and above that seen in the absence of myelin. This may be because the molecule was disinhibiting inhibitors other than myelin-related molecules.

Hence, it is especially preferred that the siNA molecule comprises SEQ ID No.12.

Therefore, the inventors have shown that gene silencing with molecules according to the invention may be used to improve neuron survival and axon growth. It is preferred that the molecules are siRNA molecules which mediate knock down of either NgR, p75$^{NTR}$ and/or Rho-A. It is most preferred that the molecules according to the invention are used in conjunction with an NTF (e.g. FGF2). When this is the case the molecules according to the invention are very effect for disinhibiting NTF stimulated axon growth and, surprisingly neuron survival. The inventors found that knockdown of p75$^{NTR}$, NgR, and Rho-A in FGF2-stimulated DRGN promoted 5-, 3.5- and 6.5-fold increased neurite outgrowth respectively in the presence of CNS myelin. Neurites grew longer after siNA-mediated knock down of Rho-A than after knockdown of p75$^{NTR}$ and NgR. This suggests that Rho-A silencing may be a particularly effective disinhibition strategy to promote CNS axon regeneration in vivo. Accordingly, it especially preferred that the siNA molecule according to the invention is SEQ ID No.12. Without being bound by any hypothesis, the inventors believe that silencing of RhoA leads to the surprising silencing of upstream components of the signalling pathway—presumably by a yet to be defined feedback loop.

According to a fifth aspect of the invention there is provided a gene silencing molecule adapted to down-regulate expression of a gene encoding a peptide involved with the Rho-A inhibitory pathway, characterised in that the molecule is adapted to induce more neuron survival and axon growth in the presence of a neurite growth inhibitor molecule than in the absence of the inhibitor molecule.

By the expression "more neuron survival and axon growth", we mean a greater level of induction is achieved when a neurite growth inhibitor molecule is present compared to when the same neurite growth inhibitor molecule is absent.

Preferably, the molecule in accordance with the fifth aspect may be used in combination with an NTF (e.g. FGF2 or CNTF), whose activities are inhibited in the presence of neurite growth inhibitor molecules such as the previously named myelin-related molecules. The molecule according to the fifth aspect of the invention, not only reverses inhibition of the NTF-stimulated axonal growth caused by neurite growth inhibitor molecules such as the myelin-related molecules indicated, but will also surprisingly stimulate neuron survival and axon growth to a greater extent than seen in the absence of the inhibitor molecule. For instance, the effect is greater than found in control experiments in which neurites are stimulated with an NTF in the absence of a neurite growth inhibitor molecule (e.g. CNS neurons stripped of myelin).

It is preferred that the molecule according to the fifth aspect comprises an siNA molecule, and may be selected from the group of siRNA molecules with the sequences identified as SEQ ID No.2, SEQ ID No.6, or SEQ ID No.12.

Gene silencing molecules used according to any aspect of the invention are preferably nucleic acids (e.g. siRNA or antisense or ribozymes). Such molecules may (but not necessarily) be ones, which become incorporated in the DNA of cells of the subject being treated. Undifferentiated cells may be stably transformed with the gene silencing molecule leading to the production of genetically modified daughter cells (in which case regulation of expression in the subject may be required, e.g. with specific transcription factors, or gene activators).

The gene silencing molecule may be either synthesised de novo, and introduced in sufficient amounts to induce gene silencing (e.g. by RNA interference) in the target cell. Alternatively, the molecule may be produced by a micro-organism, for example, E. coli, and then introduced in sufficient amounts to induce gene silencing in the target cell.

The molecule may be produced by a vector harbouring a nucleic acid, which encodes the gene silencing sequence. The vector may comprise elements capable of controlling and/or enhancing expression of the nucleic acid. The vector may be a recombinant vector. The vector may for example comprise plasmid, cosmid, phage, or virus DNA. In addition to, or instead of using the vector to synthesise the gene silencing molecule, the vector may be used as a delivery system for transforming the target cell with the gene silencing sequence.

The recombinant vector may also include other functional elements. For instance, recombinant vectors can be designed such that the vector will autonomously replicate in the target cell. In this case, elements that induce nucleic acid replication may be required in the recombinant vector. Alternatively, the recombinant vector may be designed such that the vector and recombinant nucleic acid molecule integrates into the genome of a target cell. In this case nucleic acid sequences, which favour targeted integration (e.g. by homologous recombination) are desirable. Recombinant vectors may also have DNA coding for genes that may be used as selectable markers in the cloning process.

The recombinant vector may also comprise a promoter or regulator or enhancer to control expression of the nucleic acid as required. Tissue specific promoter/enhancer elements may be used to regulate expression of the nucleic acid in specific cell types, for example, CNS neurons. The promoter may be constitutive or inducible.

Alternatively, the gene silencing molecule may be administered to the target cell or subject with or without it being incorporated in a vector. For instance, the molecule may be incorporated within a liposome or virus particle (e.g. a retrovirus, herpes virus, pox virus, vaccina virus, adenovirus, lentovirus and the like). Alternatively a "naked" siNA or antisense molecule may be inserted into a subject's cells by a suitable means e.g. direct endocytotic uptake.

The gene silencing molecule may be transferred to the cells of a subject to be treated by either transfection, infection, microinjection, cell fusion, protoplast fusion or ballistic bombardment. For example, transfer may be by: ballistic transfection with coated gold particles; liposomes containing an siNA molecule; viral vectors comprising a gene silencing sequence (e.g. adenovirus comprising SEQ ID No.2, 6 or 12); or means of providing direct nucleic acid uptake (e.g. endocytosis) by application of the gene silencing molecule directly.

In a preferred embodiment of the present invention siNA molecules may be delivered to a target cell (whether in a vector or "naked") and may then rely upon the host cell to be replicated and thereby reach therapeutically effective levels. When this is the case the siNA is preferably incorporated in an expression cassette that will enable the siNA (e.g. SEQ ID No.2, 6 or 12) to be transcribed in the cell and then interfere with translation of the endogenous mRNA coding a protein involved in the Rho-A pathway.

It will be appreciated that the gene silencing molecules according to the present invention may be used in a monotherapy (e.g. use of siNA's according to the invention stimulate neuron survival and axon growth). However it is preferred that the molecules according to the invention may be used as an adjunct, or in combination with, known therapies used to stimulate axon growth. It is particularly preferred that the combination therapy comprises a gene silencing molecule and an NTF (e.g FGF2 or CNGF).

Gene silencing molecules according to the invention may be combined in compositions having a number of different forms depending, in particular on the manner in which the composition is to be used. Thus, for example, the composition may be in the form of a capsule, liquid, ointment, cream, gel, hydrogel, aerosol, spray, micelle, transdermal patch, liposome or any other suitable form that may be administered to a person or animal suffering from a disease state characterised by impaired axon growth. It will be appreciated that the vehicle of the composition of the invention should be one which is well tolerated by the subject to whom it is given, and preferably enables delivery of the molecule to the target site requiring axon growth and/or improved neuron survival.

Compositions comprising siNA's according to the invention may be used in a number of ways. For instance, systemic administration may be required in which case the compound may be contained within a composition that may, for example, be administered by injection into the blood stream. Injections may be intravenous (bolus or infusion), subcutaneous (bolus or infusion), intraventricular or subarachnoidal.

The compounds may be administered by inhalation (e.g. intranasally).

Gene silencing molecules may also be incorporated within a slow or delayed release device. Such devices may, for example, be inserted at the site of a CNS lesion, and the molecule may be released over weeks or months. Such devices may be particularly advantageous when long term treatment with a gene silencing molecule according to the invention is required and which would normally require frequent administration (e.g. at least daily injection).

It will be appreciated that the amount of a gene silencing molecule that is required is determined by its biological activity and bioavailability which in turn depends on the mode of administration, the physicochemical properties of the molecule employed and whether it is being used as a monotherapy or in a combined therapy with an NTF. The frequency of administration will also be influenced by the above-mentioned factors and particularly the half-life of the molecule within the subject being treated.

Optimal dosages to be administered may be determined by those skilled in the art, and will vary with the particular gene silencing molecule in use, the strength of the preparation, the mode of administration, and the advancement or severity of the disease condition, and the urgency of the requirement for axon growth. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations for use according to the invention and precise therapeutic regimes (such as daily doses of the gene silencing molecule and the frequency of administration).

Generally, a daily dose of between 0.01 µg/kg of body weight and 0.5 g/kg of body weight of a gene silencing molecule according to the invention may be used for the stimulation of axon growth (and promoting neuron survival), depending upon which specific gene silencing molecule is used. More preferably, the daily dose is between 0.01 mg/kg of body weight and 200 mg/kg of body weight, and more preferably, between approximately 0.1 mg/kg and 100 mg/kg, and even more preferably, between about 1 mg/kg and 10 mg/kg.

When the molecule (e.g. siNA or antisense) is delivered to a cell (and de novo synthesis is not required in the target cell), daily doses may be given as a single administration (e.g. a single daily injection). Typically, a therapeutically effective dosage should provide about 1 ng to 100 µg/kg of the gene silencing molecule per single dose, and preferably, 2 ng to 50 ng per dose.

Alternatively, the molecule may require administration twice or more times during a day. As an example, siNA's according to the invention may be administered as two (or more depending upon the severity of the condition) daily doses of between 0.1 mg/kg and 10 mg/kg (i.e. assuming a body weight of 70 kg). A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

According to a sixth aspect, there is provided a composition comprising a therapeutically effective amount of a gene silencing molecule according to the first aspect of the invention, and a pharmaceutically acceptable vehicle.

In one embodiment, the composition according to the sixth aspect of the invention may comprise about 0.01 µg and 0.5 g of the gene silencing molecule. More preferably, the amount of the composition is between 0.01 mg and 200 mg, and more preferably, between approximately 0.1 mg and 100 mg, and even more preferably, between about 1 mg and 10 mg of the gene silencing molecule. Most preferably, the composition comprises between approximately 2 mg and 5 mg of the gene silencing molecule.

Preferably, the composition comprises approximately 0.1% (w/w) to 90% (w/w) of the gene silencing molecule, and more preferably, 1% (w/w) to 10% (w/w) of the gene silencing molecule. The rest of the composition may comprise the vehicle.

This invention provides a process for making a pharmaceutical composition comprising combining a therapeutically effective amount of a gene silencing molecule according to the invention and a pharmaceutically acceptable vehicle.

A "therapeutically effective amount" is any amount of a molecule according to the first or fourth aspect of the invention which, when administered to a subject stimulates axon growth and neuron survival.

A "subject" may be a vertebrate, mammal, domestic animal or human being.

A "pharmaceutically acceptable vehicle" as referred to herein is any physiological vehicle known to those of ordinary skill in the art useful in formulating pharmaceutical compositions.

In a preferred embodiment, the pharmaceutical vehicle is a liquid and the pharmaceutical composition is in the form of a solution. In another embodiment, the pharmaceutical vehicle is a gel and the composition is in the form of a cream or the like.

Liquid pharmaceutical compositions which are sterile solutions or suspensions can be utilized by for example, intramuscular, intrathecal, epidural, intraperitoneal, intravenous and particularly subcutaneous, intracerebral or intracerebroventricular injection. The siNA may be prepared as a sterile solid composition that may be dissolved or suspended at the time of administration using sterile water, saline, or other appropriate sterile injectable medium. Vehicles are intended to include necessary and inert binders, suspending agents, lubricants, flavourants, sweeteners, preservatives, dyes, and coatings.

The combination of a gene silencing molecule and an NTF represent an important feature of the present invention. The inventors have therefore found that the combination of these two active ingredients is particularly beneficial for inducing neuron growth and promoting cell survival in injured tissues.

Therefore, according to a seventh aspect of the invention, there is provided a composition for promoting neuron survival and axon growth, the composition comprising a gene silencing molecule adapted to down-regulate expression of a gene encoding a peptide involved with the Rho-A inhibitory pathway, and a neurotrophic growth factor.

The composition according to the seventh aspect may be used to treat individuals suffering from CNS injury.

According to an eighth aspect, there is provided a method of promoting neuron survival and axon growth in a subject, the method comprising administering to a subject in need of such treatment a composition comprising a gene silencing molecule adapted to down-regulate expression of a gene encoding a peptide involved with the Rho-A inhibitory pathway, and a NTF.

Examples of suitable neurotrophic growth factors may include CNTF, FGF2, NGF, NT-3, NT-4, BDNF, GDNF, FGF-1, FGF-5, CT-1, CDF, insulin, IGF-1, IGF-2, IL-6, LIF, NPF, PDGF, PN-1, S-100, TGF-β, and VIP and the like (Oppenheim, 1996, Neuron 17:195-197).

The amount of NTF may be between approximately 0.01 µg/kg of body weight and 0.5 g/kg of body weight, more preferably, about 0.1 mg/kg and 10 mg/kg.

The gene silencing molecule may comprise an antisense molecule or a short interfering nucleic acid (siNA).

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which:—

FIG. 1 shows knock down of $p75^{NTR}$ and Rho-A in dissociated retinal cultures after siRNA treatment;

FIG. 2 shows that FGF2 promotes neurite outgrowth in DRGN cultures;

FIG. 3 shows that CNS myelin blocks FGF2-promoted DRGN neurite outgrowth;

EXAMPLE 1

Materials and Methods

Adult Retinal Cultures

Figure 4:
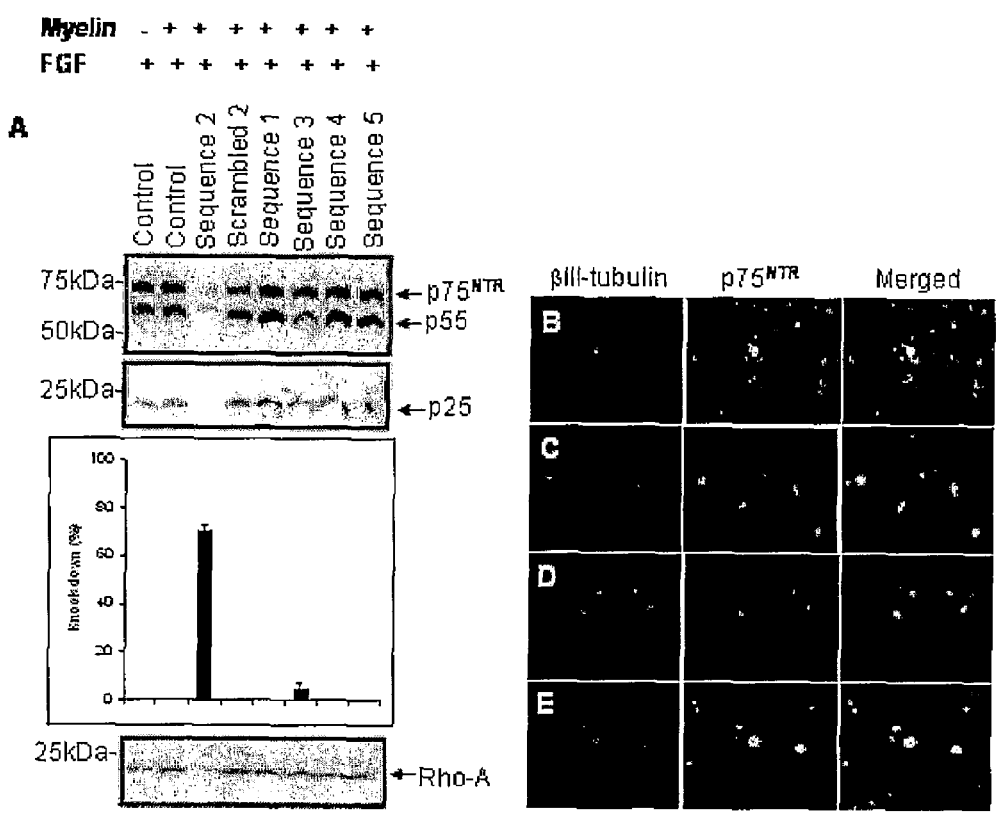
FIG. 4 shows siRNA-mediated knock down by $p75^{NTR}$ of FGF2-stimulated DRGN in the presence of CNS myelin.

Adult rats (6-8 weeks old) were killed by cervical dislocation and retinae removed by dissection and dissociated using a papain system according to the manufacturers protocol (Worthington Biochem, New Jersey, USA). $2 \times 10^6$ dissociated retinal cells containing RGC were cultured on glass coverslips precoated with 100 µg/ml poly-D-lysine (Sigma, Dorset, UK) and 20 µg/ml merosin (Chemicon, Harrow, UK) in 4-well tissue culture plates (Nunc, UK) in supplemented Neurobasal-A (Invitrogen) medium for 4 d at 37° C. in a humidified 5% $CO_2$ atmosphere.

siRNA Preparation and Transfection

To design target-specific siRNA duplex, we selected 5 siRNA sequences directed against $p75^{NTR}$ using criteria set out by Elbashir and co-workers (Nature 411: 494-498) from the open reading frame of rat $p75^{NTR}$ mRNA, NCBI accession number NM012610. Oligonucleotide templates and control-scrambled sequences were chemically synthesised (Alta Biosciences, University of Birmingham, UK) and siRNA sequences constructed using Silencer siRNA Construction kit (Ambion, Texas, USA).

The siRNA sequences used were:—

```
p75^NTR sequences:-
Sequence 1,   5'-AACCTCATTCCTGTCTATTGC-3';

Sequence 2,   5'-AACGCTTGATGCCCTTTTAGC-3';

Sequence 3,   5'-AAGAGACCAGGAGCATTGTAC-3';

Sequence 4,   5'-AAGAACCAGAGCCATGCACTC-3'
and

Sequence 5,   5'-AAGCGGAGCGCTGACGCCGGA-3'.

The scrambled sequences were:-
Antisense     5'-AATCGCATGCGTTCCATTTCGCCTGTCTC-3';

Sense         5'-AACGAAATGGAACGCATGCGACCTGTCTC-3'.
```

RGC were transfected with siRNA using Oligofectamine reagent (Invitrogen) in 4-well tissue culture plates (Nunc) according to the manufacturers instructions (Invitrogen). After 5 h of transfection, supplemented Neurobasal-A was added and incubated for a further 72 h in the presence/absence of CNS myelin (gift from N. Gregson, Kings College London, UK) before cell lysis and immunohistochemistry.

Antibodies

Monoclonal β-III tubulin (1:100) and polyclonal anti-$p75^{NTR}$ (1:500) were both from Sigma, Poole, UK, Monoclonal 192-Ig (1:100 for immunohistochemistry and 1:500 for Western Blots) was purchased from Oncogene Research Products, San Diego, USA. Goat anti human NgR (1:100 for Western blots) and monoclonal anti human Rho-A (26C4) were used to localise Rho-A by immunohistochemistry (1:200) and Western blots (1:200) (Santa Cruz, Calif., USA).

Tissue Preparation and Immunohistochemistry

Groups of at least 3 rats were killed by anaesthetic overdose and their retinae and Optic Nerve (ON) excised, embedded in OCT (Miles Inc, Calif., USA) and frozen in liquid nitrogen. Longitudinal cryostat sections, 10 µm thick, were cut through ON and retinae (Bright Instrument Co. Ltd., Cambridgeshire, UK) at −20° C., collected onto Vectabond coated slides (Vector Laboratories, Cambridgeshire, UK), air dried and processed for immunohistochemistry as previously described (Mol Cell Neurosci 21: 301-311). Cultured retinal cells were fixed in 4% paraformaldehyde and also processed as previously described (Lorber et al., 2002, Mol Cell Neurosci 21:301-311).

Neurite Outgrowth Measurement

Neurite outgrowth was measured from captured images of βIII-tubulin immunostained RGC by tracing each neurite using Axiovision software (Zeiss, Hertifordshire, UK) and measuring the longest neurite for 50 RGC in each coverslip (n=3, 3 independent experiments). The means neurite length was then calculated.

Protein Extraction and Western Blotting

At 0, 6, 8 and 20 d following ON crush, rats in each treatment group were killed and proteins from 6 pooled ON was extracted and processed for Western blotting as previously described (J Biol Chem 277: 32820-32829). To determine levels of $p75^{NTR}$ in siRNA treated RGC cultures by Western blotting, $6\times10^6$ cells/siRNA were lysed and blotted as described previously (Winton et al., 2002, J Biol Chem. 157:565-570).

Statistical Analysis

Sample means were calculated and analysed for significance using GraphPad Prism (GraphPad Software Inc., Version 4.0, San Diego, USA) by one-way analysis of variance (ANOVA) followed by post-hoc testing with Dunnett's method.

Results siRNA-Mediated Knockdown of $p75^{NTR}$ Downregulates Rho-A and Enhances CNTF-Stimulated Neurite Outgrowth in the Presence of Inhibitory CNS Myelin The inventors used primary cultures of dissociated RGC to set up an in vitro model of CNS injury and found that 100 ng/ml of CNTF, a non-Trk-dependent neurotrophin, promoted optimal RGC neurite outgrowth and that this CNTF-mediated outgrowth was inhibited by 10 μg/ml of rat CNS myelin (not shown). Knock down of $p75^{NTR}$ was achieved with siRNA $p75^{NTR}$ in CNTF-stimulated RGC growing in the presence of myelin, and the results are shown in FIG. 1, in which:—

(a) Shows complete knock down with the $p75^{NTR}$ siRNA identified as SEQ ID No. 2. and 'partial' knock down with the other siRNA sequences of $p75^{NTR}$, together with a concomitant suppression of Rho-A activation when RGC are stimulated with CNTF in the presence of myelin. Hence, all siRNA sequences exhibit efficacy. (b) A second Western blot from cultures of retinal cells shows that scrambled sequences had no effect on $p75^{NTR}$ and Rho-A, demonstrating the specificity of the effects of SEQ ID No. 2. (c) In vitro knock down, particularly with SEQ ID No. 2., restored the levels of neurite outgrowth to those seen in the absence of myelin and SEQ ID No. 2. significantly stimulated neurite outgrowth above levels seen in the absence of myelin. SEQ ID No. 2. also significantly promoted RGC survival (***P<0.0001 Sequence 2 vs CNTF in presence of myelin, ANOVA). Note that SEQ ID No. 1-5 all block the inhibitory effects of myelin. (d) Using double immunohistochemistry, βIII-tubulin$^+$ RGC grown in the presence of CNTF showed $p75^{NTR}$ immunostaining in both somata and neurites. However, in SEQ ID No. 2. -mediated $p75^{NTR}$ siRNA experiments, βIII tubulin$^+$ RGC showed either complete (somata and neurites) or partial (neurites alone) knock down of $p75^{NTR}$. Scale bars, 50 μm.

In all control cultures (untreated RGC, RGC treated with CNTF and RGC treated with CNTF and CNS myelin), significant levels of $p75^{NTR}$ and Rho-A were detected (FIG. 1a). After delivery of 5 $p75^{NTR}$ siRNA (SEQ ID Nos 1-5), SEQ ID Nos 1 and 3 induced significant knock down of $p75^{NTR}$ (70-80%, quantified by Western blot densitometry (not shown)), while SEQ ID No. 2. caused 100% knockdown of $p75^{NTR}$ and its processed forms (the extracellular domain (ECD): p55 and intracellular domain (ICD): p25 fragments) (FIG. 1a). All 5 $p75^{NTR}$ siRNA sequences tested also markedly suppressed the levels of Rho-A-GTP and the activation was completely blocked using sequences 1-3 (FIG. 1a). The control scrambled sequence for SEQ ID No. 2. caused no changes in levels of either $p75^{NTR}$, or in Rho-A activation as demonstrated in a separate Western blot (FIG. 1b).

After knock-down of $p75^{NTR}$/p5/p25 and the consequent suppression of Rho-A activation in cultured RGC by SEQ ID No. 2. siRNA, a 5-fold increase occurred in the number of RGC stimulated to grow neurites with CNTF in the presence of myelin, compared to that seen with CNTF alone in the presence of myelin (FIG. 1c), with an accompanying 5-fold promotion of RGC neurite length (FIG. 1c). Furthermore, down-regulation of $p75^{NTR}$/p55/p25 and suppression of Rho-A activation was correlated with a significant increased RGC survival after 4 days in culture (FIG. 1c). Interestingly, all 5 siRNA sequences restored CNTF-stimulated RGC neurite outgrowth, in the presence of inhibitory CNS myelin, to the levels seen with CNTF in the absence of myelin (FIG. 1c). However, SEQ ID No. 2. surprisingly enhanced RGC neurite outgrowth above the levels observed when stimulated with CNTF without CNS myelin. RGC grown in the presence of CNTF and scrambled sequence 2 showed no differences in neurite outgrowth compared to CNTF alone control (FIG. 1d).

Although the inventors do not wish to be bound by any hypothesis, they believe that these results suggest that knock-down of $p75^{NTR}$ by siRNA-mediated $p75^{NTR}$ mRNA translation silencing blocks the conversion of Rho-A GDP to Rho-A GTP, thereby enhancing CNTF-induced RGC neurite outgrowth through an inhibitory environment by preserving growth cone integrity and possibly advance via enhanced actin polymerisation.

Discussion

Each of the five siRNA molecules tested showed dis-inhibition of the RhoA inhibitory pathway. In particular, SEQ ID No. 2. was surprisingly effective stimulating more growth in the presence of inhibitory myelin than in the absence of the inhibitor. In vitro, siRNA-mediated knockdown of $p75^{NTR}$ leads to a complete blockage of activation of the downstream inhibitory signalling molecule Rho-A and CNTF-stimulated RGC survival and neurite outgrowth in the presence of CNS myelin is markedly enhanced. Whilst partially eliminating $p75^{NTR}$, $p75^{NTR}$ siRNA sequences other than SEQ ID No. 2. also led to a significant suppression of Rho-A activation and restored RGC neurite outgrowth by CNTF in the presence of CNS myelin. SEQ ID No. 2. caused complete knock down of all $p75^{NTR}$ forms and of Rho-A, in the presence of CNS myelin while enhancing neurite outgrowth two-fold over that seen in the absence of myelin. This suggests that the neurotrophic potency of CNTF is held in check by inhibitory molecules even in the absence of myelin. Although we do not wish to be bound by any hypothesis, the inventors believe that these could include CSPG, ephrins, semaphorins, etc.

In conclusion, the inventors results suggest that in NTF-stimulated regenerating RGC, an endogenous mechanism for the downregulation of $p75^{NTR}$ mediated growth cone collapse exists, involving suppression of down-stream Rho-A-mediated inhibitory signalling. This endogenous downregulation of $p75^{NTR}$ may be usefully augmented by the application $p75^{NTR}$-targeted siRNA. siRNA technology therefore provides an additional therapeutic strategy to help regenerating axons overcome the inhibitory environment of the CNS. Neuron death may be a greater barrier to successful CNS repair than first thought, and a combined therapeutic strategy that increases neuron survival as well as axon regeneration using appropriate NTFs, and molecules according to the invention are preferred ways of promoting CNS axon regeneration, cell survival, and restoring function after injury.

EXAMPLE 2

Materials and Methods

Adult DRGN cultures

L4-L7 DRG pairs were dissected from adult rats (6-8 week-old) and dissociated into single cells using a solution of Neurobasal-A (Invitrogen, Paisley, UK) containing 0.1% collagenase (Sigma, Poole, England) and 200 U/ml DNaseI (Worthington Biochem, New Jersey, USA) for 2 hr at 37° C. in a humidified atmosphere containing 5% $CO_2$, triturated several times and centrifuged through a 15% bovine serum albumin gradient to remove debris. Dissociated cells were pelleted and then resuspended in Neurobasal-A containing B27 supplement, L-glutamine and Gentimicin (supplemented Neurobasal-A, all from Invitrogen), 1,500 DRGN/well were cultured on sterile glass coverslips pre-coated with 100 μg/ml poly-D-lysine followed by 20 μg/ml Laminin-I (Sigma, Dorset, UK) in 4-well tissue culture plates (Nunc, UK), in supplemented Neurobasal-A medium, in both the presence and absence of rat CNS myelin (from Dr. Norman Gregson, King's College London, UK) for 72 hr at 37° C. in a humidified atmosphere containing 5% $CO_2$.

siRNA Preparation and Transfection

As for Example 1, siRNA directed against $p75^{NTR}$, NgR and Rho-A were designed using criteria set out by Elbashir and co-workers (Elbashir et al., 2001, supra). The coding sequence of rat $p75^{NTR}$, NgR and Rho-A was scanned to identify possible regions with a diadenine start sequence and comprising less than 50% GC content. The siRNA sequences used were:—

```
p75^NTR sequences:-
SEQ ID No. 1,  5'-AACCTCATTCCTGTCTATTGC-3';

SEQ ID No. 2,  5'-AACGCTTGATGCCCTTTTAGC-3';

SEQ ID No. 3,  5'-AAGAGACCAGGAGCATFGTAC-3';

SEQ ID No. 4,  5'-AAGAACCAGAGCCATGCACTC-3';
and

SEQ ID No. 5,  5'-AAGCGGAGCGCTGACGCCGGA-3'.

NgR sequences:-
SEQ ID No. 6,  5'-AATCTCACCATCCTGTGGCTG-3';

SEQ ID No. 7,  5'-AACCTCACGCATCTCTTTCTG-3';

SEQ ID No. 8,  5'-AATCAGCTCACTGATGAGGAG-3';

SEQ ID No. 9,  5'-AAATGCACTCAAGGGACGTGT-3';
and

SEQ ID No. 10, 5'-AATGACTCTCCATTTGGGACT-3'.

Rho-A sequences:-
SEQ ID No. 11, 5'-AAGATTATGACCGTCTGAGGC-3';

SEQ ID No. 12, 5'-AAGGATCTTCGGAATGATGAG-3';

SEQ ID No. 13, 5'-AAGGCGGGAGITAGCCAAAAT-3';

SEQ ID No. 14, 5'-AATGAAGCAGGAGCCGGTAAA-3';
and

SEQ ID No. 15, 5'-AAAGACCAAAGACGGAGTGAG-3'.
```

Selected sequences were subjected to a BLAST search (www.ncbi.nlm.nih.gov/PubMed) to ensure there was no significant homology with other genes. The sense siRNA template started with an AA dimer at the 5' end followed by the 19 nucleotide complementary to the target sequence. The 3' end of both the sense and anti-sense templates included an 8 nucleotide sequence 5'-CCTGTCTC-3' corresponding to the complementary sequence of the T7 promoter primer required for efficient transcription of the siRNA. Deprotected and desalted oligonucleotide templates and control-scrambled sequences were chemically synthesized (Alta Biosciences, University of Birmingham, UK).

```
SEQ ID No. 16: Scrambled p75NTR Seq 2:
5'-AATCGCATGCGTTCCATTTCG-3';

SEQ ID No. 17: Scrambled NgR1:
5'-AACTTCCACCATTTGGCGGTC-3';

SEQ ID No. 18: Scrambled Rho-A Seq 2:
5'-AAGAGTTCATCTGAGTAGGAG-3'
```

Oligofectamine reagent (Invitrogen) was used in 4-well tissue culture plates (Nunc) for siRNA transfection. In one tube, 0.84 μg of siRNA/well was mixed in 50 μl Opti-MEM (Invitrogen), while a second tube contained 3 μl Oligofectamine (Invitrogen) and 12 μl Opti-MEM (Invitrogen). These tubes were incubated at room temperature for 5 min before the two solutions were combined and allowed to incubate for a further 25 min at room temperature for complex formation. The entire mixture was then supplemented with Opti-MEM (Invitrogen) to the required amount to allow addition of 150 μl of transfection medium for each well of DRGN. After 5 hr of transfection, supplemented Neurobasal-A was added to the transfection media to bring the final volume to 500 μl/well and DRGN were incubated for a further 48 hr before being subjected to either cell lysis (for Western blot analysis) or immunocytochemistry.

Antibodies

Monoclonal β-III tubulin antibody (Sigma) was used at 1:100 to label DRGN neurites by immunocytochemistry (ICC) and at 1:500 in Western blots. Polyclonal anti-$p75^{NTR}$ Ab was used to identify and localise $p75^{NTR}$ (Sigma, 1:500 dilution for both Western blots and ICC). Monoclonal 192-Ig was used to identify and localise the kDa processed cytoplasmic fragment of $p75^{NTR}$ (Oncogene Research Products, San Diego, Calif., USA; 1:200 dilution for Western blotting). Rho-A (monoclonal and polyclonal Abs, 1:200 dilution of both for Western blotting and ICC) and polyclonal anti-NgR Ab (1:100 dilution for both Western blotting and ICC) were purchased from Santa Cruz Biotechnology, Calif., USA.

Immunocytochemistry

DRG cultures were fixed in 4% paraformaldehyde for 10 min (TAAB Laboratories, Berkshire, UK) prior to washing ×3 in phosphate buffered saline (PBS), blocked in PBS containing 0.5% bovine serum albumin (BSA, Sigma) and 1% Triton X-100 (Sigma), and incubated with the relevant primary antibody diluted 1:100 in PBS containing 0.5% BSA and 0.5% Tween-20 (Sigma) for 1 hr at room temperature in a humidified chamber. Cells were then washed ×3 in PBS and incubated with either Alexa Fluor 488 (Green), or Texas Red (Red) (both from Molecular Probes), diluted 1:100 in PBS-T-BSA for 1 hr at room temperature. Following further washes in PBS, coverslips were mounted in Fluor Save (Calbiochem, San Diego, USA) and viewed under a fluorescent microscope (Carl Zeiss, Welwyn-Garden City, UK).

Measurement of Neurite Outgrowth

Photomicrographs of βIII-tubulin+ immunostained DRGN neurites were captured using Axiovision Software (Carl Zeiss) from 30 randomly selected DRGN/coverslip using the measurement facilities in Axiovision. Neurite lengths were represented as mean ±SD. The software could not be used to measure neurites from siRNA knock down experiments since neurite outgrowth was extensive. In such cases, DRGN cell lysates were used to Western blot for βIII-tubulin as a measure of neurite outgrowth.

Protein Extraction and Western Blotting

To determine levels of $p75^{NTR}$, NgR and Rho-A in siRNA treated DRG cultures, cells were washed ×2 with PBS and incubated for 15 min at 37° C. with 0.25% trypsin/EDTA (Invitrogen), followed by trituration and centrifugation at 1300 rpm for 5 min. The DRG cell pellet was re-suspended in ice-cold lysis buffer containing 20 mM Tris-HCl (pH 7.4), 1 mM EDTA, 0.5 mM EGTA, 150 mM NaCl, 1% NP-40 (Sigma) and protease inhibitor cocktail (Sigma) and incubated on ice for 30 min. After a 30 min centrifugation at 13,000 rpm at 4° C., the lysates were normalised for protein concentration using a colorimetric DC protein assay (Bio-Rad, Hercules, Calif., USA). Homogenates and cell lysates were stored at −70° C. until used for Western blot analysis.

Each sample (40 μg total protein) was incubated with ×2 Laemmeli loading buffer at 90° C. for 4 m and separated on a 12% SDS-polyacrylamide gel (Invitrogen). Proteins were transferred to PVDF membranes (Millipore UK, Gloucestershire, UK), blocked for 1 hr at room temperature in Tris-buffered saline containing 0.1% Tween 20 and 5% non-fat milk. Membranes were blotted overnight for the relevant antibody. For detection, an enhanced chemiluminescence (ECL) system (Amersham, Buckinghamshire, UK) and HRP-conjugated secondary antibody (1:1,000, Amersham) was used. Each blot was stripped and re-probed with relevant antibodies thereafter.

DRGN Survival

Following siRNA-mediated knock down, the number of βIII-tubulin⁺ DRGN was counted under a fluorescent microscope by scanning the whole area of 9 coverslips per siRNA. The mean number of DRGN/coverslip was calculated and analysed statistically as described below.

Densitometry

Western blots and antibody evaluation for each siRNA were performed ×3 in 3 separate experiments and, where relevant, blots were quantified by densitometry using Scion-Image software (Scion Corporation/NIH Image, USA).

Statistical Analysis

Sample means were calculated and analysed for significance using GraphPad Prism (GraphPad Software Inc., Version 4.0, San Diego, USA) by one-way analysis of variance (ANOVA) followed by post-hoc testing with Dunnett's method to identify statistically significant groups.

Results

FGF2 Promotes DRGN Neurite Outgrowth In order to test the potency of the selected siRNA sequences, the inventors first set up an in vitro model in which FGF2, a non-Trk-dependent neurotrophic factor, was used to stimulate neurite outgrowth in DRGN, and the results are shown in FIG. 2, in which:—

A, No FGF2; B, 1 ng/ml FGF2; C, 10 ng/ml FGF2; D, 100 ng/ml FGF2; E, 200 ng/ml FGF2 causes a dose-dependent increase in DRGN neurite length; and F, quantification of βIII-tubulin⁺ mean ±SD neurite length by image analysis showing optimal neurite outgrowth with 10 ng/ml FGF2, after which mean neurite outgrowth decreased. ***P<0.0001, 10 ng/ml FGF2 vs 0 ng/ml).

The results show that βIII-tubulin positive DRGN neurites grew in Neurobasal-A alone, reaching an average length of 350±35 μm (as shown in FIGS. 2A and F). However, increasing concentrations of FGF2, up to 10 ng/ml, increased neurite outgrowth (FIGS. 2B, C and F). Beyond this optimal concentration, DRGN neurite outgrowth decreased (FIG. 2D-F). These results demonstrate that FGF2 can efficiently promote neurite outgrowth in DRGN in a concentration-dependant manner.

Inhibition of FGF2-Stimulated DRGN Neurite Outgrowth in CNS Myelin

The inhibition of FGF2-stimulated DRGN neurite outgrowth by CNS myelin was determined by culturing DRGN in the presence of a range of CNS myelin concentrations, and the results are shown in FIG. 3, in which:—

A, No CNS myelin; B, 100 μg/ml CNS myelin; C, 10 μg/ml CNS myelin; D, 100 μg/ml CNS myelin; E, 200 μg/ml CNS myelin causes a dose-dependent decrease in DRGN neurite length; and F, quantification of mean ±SD neurite length by image analysis showing the optimal concentration of 200 μg/ml CNS myelin for inhibition of DRGN neurite outgrowth, higher concentrations of CNS myelin (500 μg/ml) are toxic to DRGN. ***P<0.0001, 200 μg/ml vs 0 μg/ml myelin.

DRGN neurite outgrowth stimulated by 10 ng/ml FGF2 (as shown in FIG. 3A) was reduced significantly by growing DRGN in the presence of 100 μg/ml CNS myelin (FIG. 3B), while 200 μg/ml CNS myelin almost completely inhibited FGF2-mediated DRGN neurite outgrowth (FIG. 3C). Increasing the concentration of CNS myelin to 250 μg/ml (FIG. 3D) and 500 μg/ml (FIG. 3E) completely inhibited neurite outgrowth. However, since the highest concentration of CNS myelin used led to increased cell death and altered DRGN morphology, we chose 200 μg/ml myelin to provide optimal inhibition for our subsequent siRNA experiments. Quantification of neurite outgrowth by measurement of neurite length confirmed these observations (FIG. 3F) and demonstrated that FGF2-stimulated neurite outgrowth was effectively blocked by CNS myelin.

$p75^{NTR}$ siRNA Knocks Down $p75^{NTR}$ and its Fragments and Also Down Regulates Rho-A in DRGN The inventors have demonstrated in Example 1 that out of 5 selected siRNA sequences to $p75^{NTR}$ mRNA, SEQ ID No. 2 completely knocked down $p75^{NTR}$ and its processed fragments, together with downstream Rho-A in RGC (see Example 1). Western blot analysis of cell lysates from DRG cultures grown in the presence of FGF2 alone did not show any changes in $p75^{NTR}$ and Rho-A protein levels. However, $p75^{NTR}$ protein levels remained unaffected in cell lysates grown in the presence of FGF2 and CNS myelin, whilst Rho-A levels were enhanced, showing an induction of the inhibitory pathway (as shown in FIG. 4A).

In FIG. 4: A, Western blotting of cell lysates after siRNA-mediated gene silencing shows a 70% knockdown of $p75^{NTR}$ protein with down regulation of all fragments of $p75^{NTR}$ and subsequent suppression of Rho-A activation; B, Double immunocytochemistry with βIII-tubulin and $p75^{NTR}$ antibodies shows neurite outgrowth with FGF2 in the absence of CNS myelin while $p75^{NTR}$ immunostaining is localised to DRGN somata and their neurites; C, Although CNS myelin inhibits neurite outgrowth, it has no effect on $p75^{NTR}$ immunoreactivity; D, Transfection of DRGN with $p75^{NTR}$ sequence 2 caused a marked reduction in immunoreactivity to $p75^{NTR}$ associated with significant (P<0.0001 versus $p75^{NTR}$ scrambled sequence 2) neurite outgrowth; E, In the presence of the scrambled sequence to $p75^{NTR}$ sequence 2, immunoreactivity to $p75^{NTR}$ is maintained without any apparent neurite outgrowth.

When DRGN were transfected with the same 5 siRNA sequences to $p75^{NTR}$ mRNA as were used for RGC (see Example 1), sequence 2 again caused the greatest knock down of $p75^{NTR}$ and its processed fragments, p55 and p25 with 70% efficiency (P<0.0001 versus scrambled 2) (FIG. 4A). The knock down observed with SEQ ID No. 2 was specific, since a scrambled version of sequence 2 had no effect on $p75^{NTR}$ knock down. When the blots were stripped and re-probed for Rho-A, almost complete knock down of Rho-A was also achieved with $p75^{NTR}$ siRNA SEQ ID No. 2. $p75^{NTR}$ immunoreactivity was present in βIII-tubulin⁺ DRGN together with modest neurite outgrowth in the presence of FGF2 without CNS myelin (FIG. 4B). $p75^{NTR}$ immunoreactivity of DRGN somata and neurites was not affected by the presence of CNS myelin and FGF2 in combination, but neurite outgrowth was significantly reduced (FIG. 4C).

However, there was marked reduction in $p75^{NTR}$ immunoreactivity in DRGN grown in the presence of $p75^{NTR}$ siRNA sequence 2, with CNS myelin and FGF2, and neurite outgrowth was enhanced (FIG. 4D). The scrambled control sequence 2 showed no changes in $p75^{NTR}$ immunoreactivity and no neurite outgrowth in the presence of FGF2 and CNS myelin (FIG. 4E), confirming that the biological response of $p75^{NTR}$ siRNA SEQ ID No. 2-mediated knock down was a specific response of the siRNA which also caused efficient knock down of the downstream inhibitory signalling molecule, Rho-A.

NgR siRNA Significantly Knocks Down NgR in DRGN

Figure 5:
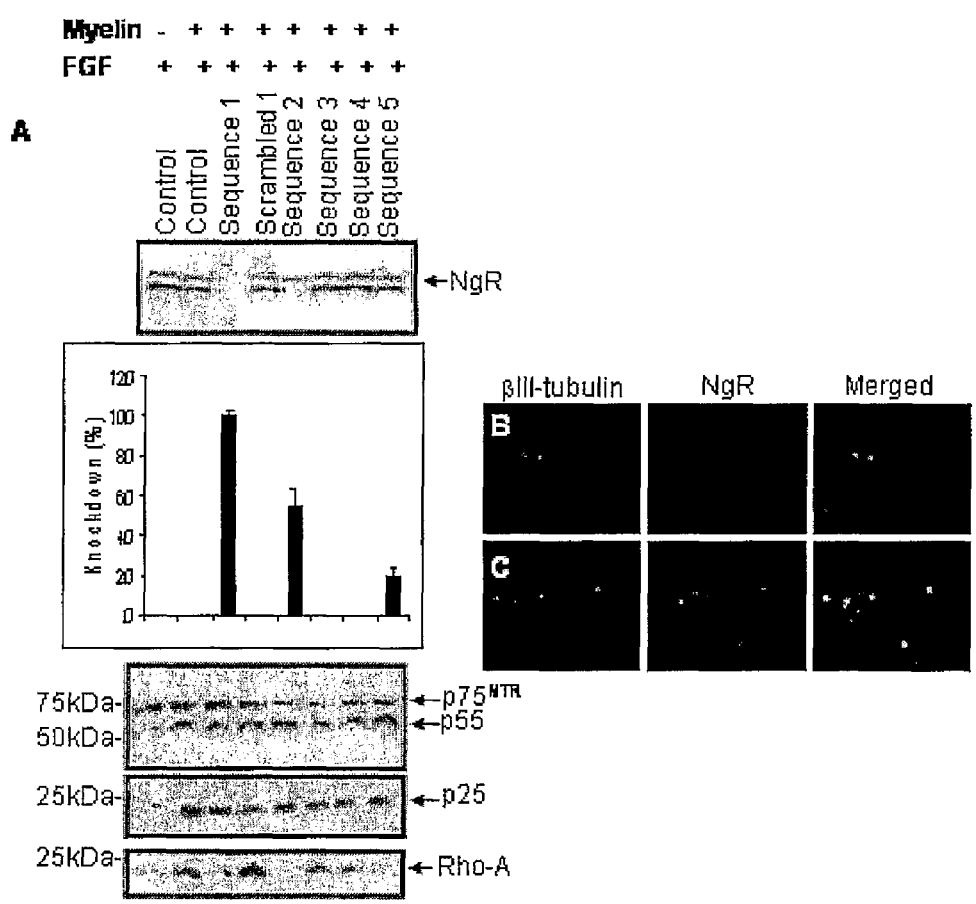
FIG. 5 shows siRNA-mediated knock down of NgR in FGF2-stimulated DRGN in the presence of myelin.

The inventors tested 5 sequences of siRNA (SEQ ID No. 6-10) against NgR mRNA for knock down of NgR in DRGN and the results are shown in FIG. 5, in which:—

A, Western blotting of cell lysates after siRNA-mediated gene silencing shows a 100%, 55% and 18% knock down of NgR protein using siRNA SEQ ID No. 6, 7 and 10, respectively; B, Transfection of DRGN with NgR siRNA SEQ ID No. 6 causes a significant reduction in immunoreactivity while promoting significant neurite outgrowth; and C, However, double immunocytochemistry with βIII-tubulin and NgR antibodies in DRGN transfected with scrambled sequence 1 revealed no neurite outgrowth and no change in NgR immunoreactivity.

The inventors showed that SEQ ID No. 6 completely knocked down NgR (100% knock down, P<0.0001 versus scrambled 1) as shown in FIG. 5A in the presence of FGF2 and CNS myelin. A scrambled version of siRNA NgR SEQ ID No. 6 had no effect on NgR levels, demonstrating the specificity of SEQ ID No. 6 siRNA. Following NgR knock down there was no modulation in $p75^{NTR}$ and its fragments, however, levels of active Rho-A were reduced in samples in which significant knock down was achieved (FIG. 5A). NgR immunoreactivity was markedly reduced in DRGN transfected with NgR siRNA SEQ ID No. 6, while the growth of βIII-tubulin⁺ neurites was enhanced after stimulation with FGF2 in the presence of CNS myelin (FIG. 5B). The scrambled NgR SEQ ID No. 6 had no effect on NgR immunoreactivity and neurite outgrowth of DRGN in the presence of FGF2 and CNS myelin (FIG. 5C).

Rho-A siRNA Significantly Knocks Down Rho-A in DRGN

Figure 6:
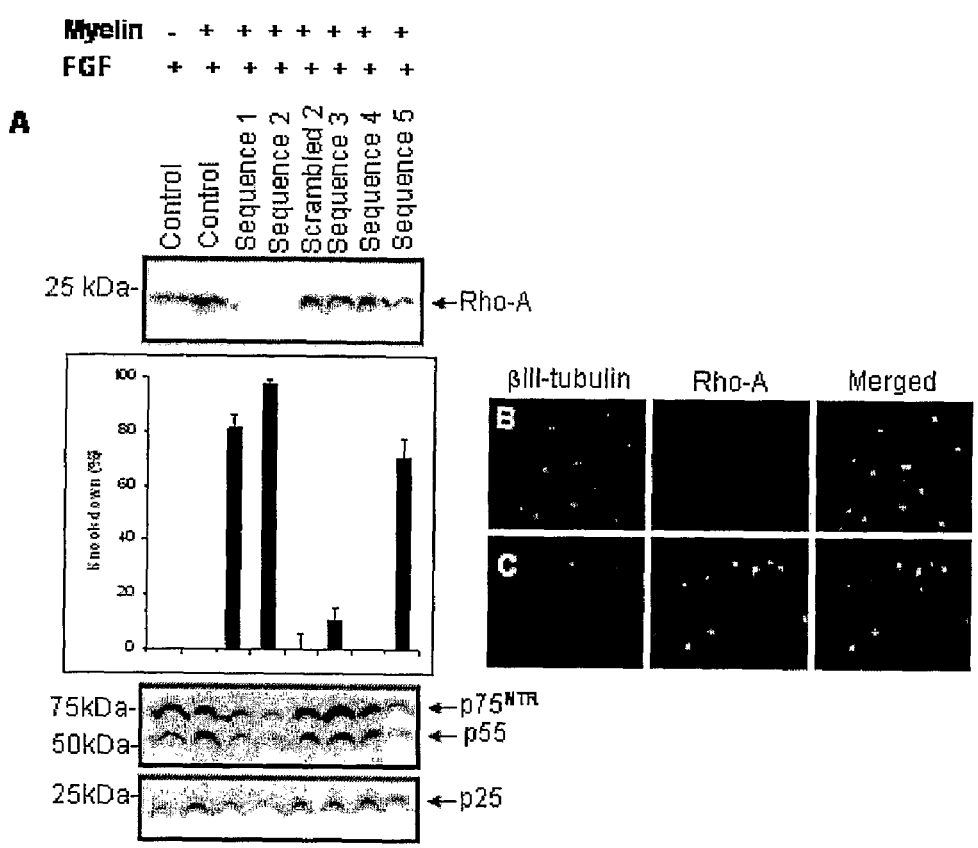
FIG. 6 shows siRNA-meditated knock down of Rho-A in FGF2-stimulated DRGN in the presence of myelin.

The inventors next constructed 5 sequences of siRNA (SEQ ID No. 11-15) to the downstream inhibitory signalling molecule Rho-A and tested their ability to knock down Rho-A in DRGN, and the results are shown in FIG. 6, in which:—

A, Western blotting of cell lysates after siRNA-mediated gene silencing shows an 80%, 100%, 10% and 70% knock down of Rho-A protein using Rho-A siRNA SEQ ID Nos. 11, 12, 13 and 15, respectively. Also apparent is a concomitant reduction in full length and processed forms of $p75^{NTR}$, B, DRGN transfected with SEQ ID No. 12 had reduced Rho-A immunoreactivity, and robust neurite outgrowth; and C, Double immunocytochemistry with βIII-tubulin and NgR antibodies in DRGN transfected with scrambled SEQ ID No. 12, however, shows no neurite outgrowth and no change in Rho-A immunoreactivity:

SEQ ID No. 12 completely knocked down Rho-A (100% knock down, P<0.0001 versus scrambled sequence 12) protein in DRGN stimulated with FGF2 in the presence of CNS myelin, while a scrambled version had no effect (FIG. 6A). siRNA-mediated knock down of Rho-A was correlated with marked knock down of $p75^{NTR}$ and its fragments, p55 and p25 (FIG. 6A). Rho-A siRNA SEQ ID No. 12 almost completely abolished Rho-A immunoreactivity in βIII-tubulin⁺ DRGN and led to greater FGF2-stimulated neurite outgrowth, in the presence of CNS myelin, than any other siRNA sequences tested (FIG. 6B). The scrambled Rho-A SEQ ID No. 2 had no effect on either Rho-A immunocytochemistry, or neurite outgrowth of DRGN (FIG. 6C).

Quantification of DRGN Neurite Outgrowth from Western Blots of βIII-Tubulin

Figure 7:
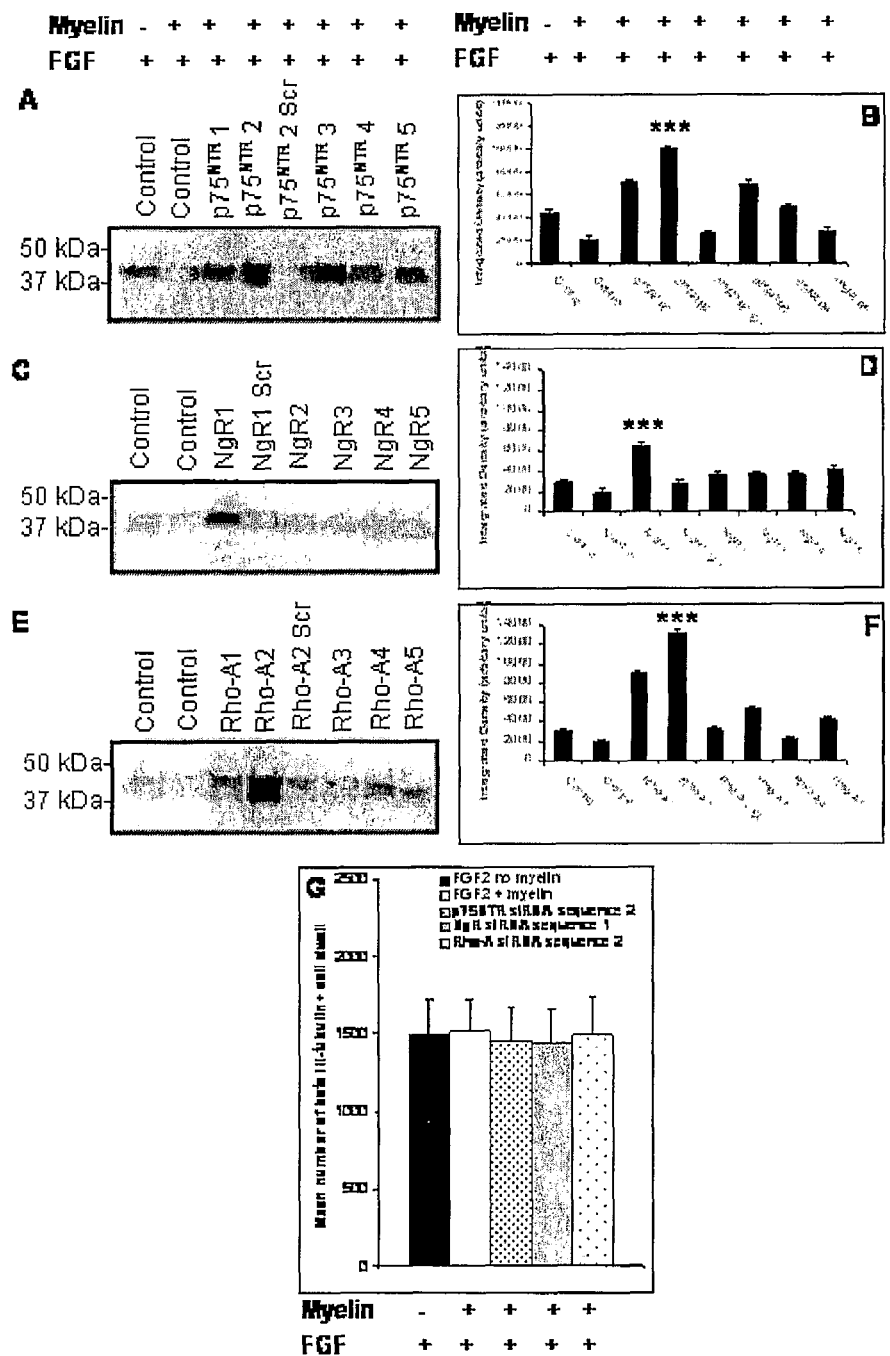
FIG. 7 shows Western blot and densitometric quantification of βIII-tubulin in DRG cultures as a correlate of FGF2-stimulated DRGN neurite outgrowth in the presence of CNS myelin after siRNA-mediated knock down of $p75^{NTR}$, NgR and Rho-A.

It was difficult to use the Axiovision software to measure the length of neurites observed with siRNA-mediated knock down of $p75^{NTR}$, NgR and Rho-A, since many DRGN grew more than one neurite, and these were interspersed with neurites from neighbouring DRGN. Densitometric analysis of Western blots of βIII-tubulin was, therefore, used to estimate neurite outgrowth, and the results are shown in FIG. 7, in which:—

A and B, Significantly higher amounts of βIII-tubulin protein is detected in DRGN transfected with $p75^{NTR}$ siRNA SEQ ID No. 2 than with either scrambled, or any of the other siRNA sequences (P<0.0001, ANOVA), revealing a 5-fold increase compared to DRGN grown in the presence of FGF2 and CNS myelin alone; C and D, Using siRNA to NgR, significantly higher amounts of βIII-tubulin protein are detected in DRGN transfected with SEQ ID No. 6 than with the either scrambled, or any of the other siRNA sequences (P<0.0001, ANOVA), revealing a 3-fold increase compared to DRGN grown in the presence of FGF2 and myelin alone; E and F, Using siRNA to Rho-A, significantly higher amounts of βIII-tubulin protein are detected in DRGN transfected with Rho-A SEQ ID No. 12 than with the either scrambled or, any of the other siRNA sequences (P<0.0001, ANOVA), revealing a 6.5-fold increase compared to DRGN grown in the presence of FGF2 and myelin alone. The greatest amount of βIII-tubulin protein (reflecting the most robust neurite outgrowth) is detected in DRGN transfected with Rho-A siRNA SEQ ID No. 12; and G, Counting the number of βIII-tubulin⁺ DRGN as a measure of cell survival, revealed no significant changes following siRNA-mediated knock down with $p75^{NTR}$, NgR or Rho-A. ***P<0.0001 vs control DRGN with FGF2 and myelin.

FGF2-stimulated neurite outgrowth in the presence of CNS myelin was enhanced 5-fold when siRNA SEQ ID No. 2 was used to knock down $p75^{NTR}$ (FIGS. 7A and B), 3.5-fold when siRNA SEQ ID No. 6 was used to knock down NgR (FIGS. 7C and D) and 6.5-fold siRNA SEQ ID No. 12 was used to knock down Rho A (FIGS. 6E and F). FGF2-stimulated βIII-tubulin levels were further increased after Rho-A knock down than those seen after $p75^{NTR}$ knock down. These results show that blocking Rho-A optimally disinhibits FGF2-stimulated DRGN neurite outgrowth in the presence of CNS myelin.

DRGN Survival After Knock Down of $p75^{NTR}$, NgR and Rho-A

The number of βIII-tubulin⁺ DRGN present in cultures after knock down of $p75^{NTR}$, NgR and Rho-A, stimulated with FGF2 in the presence of myelin, remained unaffected (FIG. 7G). This suggested that knock down of either $p75^{NTR}$, NgR, or Rho-A had no adverse effects on FGF2-stimulated DRGN neurite outgrowth in the presence of CNS myelin.

Discussion

The inventor's axon growth disinhibition strategy uses siRNA to target the inhibitory signalling cascade, rather than the inhibitory ligands. Knock down of $p75^{NTR}$, NgR and Rho-A in FGF2-stimulated DRGN all led to disinhibition of neurite outgrowth in the presence of CNS inhibitory myelin, with knock down of Rho-A causing the most pronounced effect. The most effective siRNA, Rho-A SEQ ID No. 12, promoted FGF2-stimulated neurite outgrowth 6.5-fold over that observed with FGF2 in the presence of CNS myelin, and 1.5-fold over that observed with siRNA $p75^{NTR}$ SEQ ID No. 2. Interestingly, siRNA-mediated knock down of $p75^{NTR}$ also caused complete knock down of Rho-A, while siRNA-mediated knock down of total Rho-A conversely caused modest, but nonetheless significant, knock down of $p75^{NTR}$ in DRGN. Knock down of NgR enhanced neurite outgrowth the least, increasing FGF2-stimulated neurite outgrowth 3.5-fold when compared to DRGN grown in the presence of CNS myelin.

siRNA-Mediated Knock Down of $p75^{NTR}$

The inventors have demonstrated that siRNA-mediated gene silencing of $p75^{NTR}$ disinhibits neurite outgrowth in RGC in the presence of CNS myelin (Example 1). The inventors have also shown that $p75^{NTR}$ knock down led to suppression of Rho-A activation, thereby indicating suppression of inhibitory signalling (Example 2). Here, the inventors used the same siRNA sequences to study the effects of $p75^{NTR}$ gene silencing in DRGN in vitro. The observation that knock NTR down of p75 together with its fragments and subsequent suppression of Rho-A activation enhanced FGF2-stimulated DRGN neurite outgrowth in the presence of myelin, supports the hypothesis that $p75^{NTR}$ is required by the inhibitory ligand binding molecule NgR, to transduce its signals in multiple neuronal cell types.

In conclusion, the results demonstrate that knock down of $p75^{NTR}$ has a significant beneficial impact on neurotrophin-stimulated (CNTF) neurite outgrowth of RGC in the presence of a putative inhibitory environment (myelin). Furthermore, knock down of NgR, $p75^{NTR}$ and Rho-A have a significant beneficial impact on neurotrophin-stimulated (FGF2) neurite outgrowth of DRGN in the presence of a putative inhibitory environment. This implies that disinhibition of neurite outgrowth by a neurotrophin-stimulated mechanisms could be a universal phenomena and that siRNA can augment the process. The results are encouraging for disinhibition strategies and suggests that RNAi against downstream signalling molecules is most beneficial in promoting optimal CNS axon regeneration.

The invention claimed is:

1. A gene silencing molecule adapted to down-regulate expression of a gene encoding a peptide involved with the Rho-A inhibitory pathway;
wherein the gene silencing molecule is a short interfering nucleic acid (siNA) comprising:

```
5'-AAGATTATGACCGTCTGAGGC-3';        (SEQ ID No. 11)
or

5'-AAGGATCTTCGGAATGATGAG-3'.        (SEQ ID No. 12)
```

2. A gene silencing molecule according to claim 1, wherein the siNA molecule comprises an siRNA molecule.

3. A gene silencing molecule according to claim 2, wherein the siNA molecule comprises between approximately 5 bp and 50 bp.

4. A gene silencing molecule according to claim 2, wherein the siNA molecule comprises less than 50% GC content.

5. A gene silencing molecule according to claim 1, wherein the gene silencing molecule comprises a sequence identified as SEQ ID No.12.

6. A gene silencing molecule according to claim 1, wherein the gene silencing molecule is used in combination with a molecule, which simulates growth of neurites.

7. A gene silencing molecule according to claim 6, wherein the molecule, which simulates growth of neurites, comprises a neurotrophic factor (NTF).

8. A gene silencing molecule according to claim 7, wherein the NTF is independently selected from a group consisting of CNTF, FGF2, NGF, NT-3, NT-4, BDNF, GDNF, FGF-1, FGF-5, CT-1, CDF, insulin, IGF-1, IGF-2, IL-6, LIF, NPF, PDGF, PN-1, S-100, TGF-β, and VIP, and the like.

9. A gene silencing molecule according to claim 8, wherein the NTF is Ciliary Neurotrophic Factor (CNTF) or Fibroblast Growth Factor 2 (FGF2).

10. A medicament comprising a gene silencing molecule according to claim 1.

11. A gene silencing molecule according to claim 1, wherein the molecule is adapted to induce more neuron survival and axon growth in the presence of a neurite growth inhibitor molecule than in the absence of the inhibitor molecule.

12. A composition comprising a therapeutically effective amount of a gene silencing molecule according to claim 1, and a pharmaceutically acceptable vehicle.

13. A composition for promoting neuron survival and axon growth, the composition comprising a gene silencing molecule according to claim 1, and a neurotrophic growth factor.

14. A composition according to claim 13, wherein the NTF is independently selected from a group consisting of CNTF, FGF2, NGF, NT-3, NT-4, BDNF, GDNF, FGF-1, FGF-5, CT-1, CDF, insulin, IGF-1, IGF-2, IL-6, LIF, NPF, PDGF, PN-1, S-100, TGF-$\beta$, and VIP.

* * * * *